(12) United States Patent
Senzig et al.

(10) Patent No.: US 11,557,069 B2
(45) Date of Patent: Jan. 17, 2023

(54) SYSTEM AND METHOD FOR ESTIMATING VASCULAR FLOW USING CT IMAGING

(71) Applicant: General Electric Company, Schenectady, NY (US)

(72) Inventors: Robert F. Senzig, Germantown, WI (US); Ravikanth Avancha, Niskayuna, NY (US); Bijan Dorri, Hartland, WI (US); Sandeep Dutta, Waukesha, WI (US); Steven J. Gray, Elm Grove, WI (US); Jiang Hsieh, Brookfield, WI (US); John Irvin Jackson, Brookfield, WI (US); Giridhar Jothiprasad, Clifton Park, NY (US); Paul Edgar Licato, Wauwatosa, WI (US); Darin Robert Okerlund, Muskego, WI (US); Toshihiro Rifu, Milwaukee, WI (US); Saad Ahmed Sirohey, Pewaukee, WI (US); Basel Taha, Madison, WI (US); Peter Michael Edic, Albany, NY (US); Jerome Knoplioch, Neuilly sur Seine (FR); Rahul Bhotika, Albany, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1066 days.

(21) Appl. No.: 16/222,586

(22) Filed: Dec. 17, 2018

(65) Prior Publication Data
US 2019/0122401 A1    Apr. 25, 2019

Related U.S. Application Data

(62) Division of application No. 13/425,724, filed on Mar. 21, 2012, now Pat. No. 10,186,056.

(Continued)

(51) Int. Cl.
*A61B 5/00* (2006.01)
*G06T 11/00* (2006.01)
(Continued)

(52) U.S. Cl.
CPC ............ *G06T 11/008* (2013.01); *A61B 6/032* (2013.01); *A61B 6/481* (2013.01); *A61B 6/503* (2013.01);
(Continued)

(58) Field of Classification Search
IPC .................... A61B 6/032,6/503, 6/481, 6/5294, A61B 6/507
See application file for complete search history.

(56) References Cited

U.S. PATENT DOCUMENTS

| 5,769,870 A | 6/1998 | Salahieh et al. |
| 5,925,054 A | 7/1999 | Taylor et al. |

(Continued)

OTHER PUBLICATIONS

Antiga (patent specific modeling of geometry and blood flow) (Year: 1999).*

(Continued)

*Primary Examiner* — Joel F Brutus
(74) *Attorney, Agent, or Firm* — Fletcher Yoder P.C.

(57) ABSTRACT

A system and method for estimating vascular flow using CT imaging include a computer readable storage medium having stored thereon a computer program comprising instructions, which, when executed by a computer, cause the computer to acquire a first set of data comprising anatomical information of an imaging subject, the anatomical information comprises information of at least one vessel. The instructions further cause the computer to process the anatomical information to generate an image volume comprising the at least one vessel, generate hemodynamic information based on the image volume, and acquire a second set of (Continued)

data of the imaging subject. The computer is also caused to generate an image comprising the hemodynamic information in combination with a visualization based on the second set of data.

15 Claims, 5 Drawing Sheets

Related U.S. Application Data (60) Provisional application No. 61/454,646, filed on Mar. 21, 2011.

(51) Int. Cl.
*A61B 6/03* (2006.01)
*A61B 6/00* (2006.01)
*G06T 7/00* (2017.01)
*G16Z 99/00* (2019.01)

(52) U.S. Cl.
CPC ............ *A61B 6/504* (2013.01); *A61B 6/507* (2013.01); *A61B 6/5217* (2013.01); *A61B 6/5294* (2013.01); *G06T 7/0016* (2013.01); *G16Z 99/00* (2019.02); *A61B 6/482* (2013.01); *G06T 2207/10081* (2013.01); *G06T 2207/30104* (2013.01); *G06T 2211/404* (2013.01)

(56) References Cited

U.S. PATENT DOCUMENTS

| | | | |
|---|---|---|---|
| 6,071,297 | A | 6/2000 | Salahieh et al. |
| 6,214,022 | B1 | 4/2001 | Taylor et al. |
| 2003/0083565 | A1* | 5/2003 | Toth .................. G06V 10/987 600/407 |
| 2004/0249270 | A1* | 12/2004 | Kondo ................ G06T 7/12 382/128 |
| 2005/0063611 | A1 | 3/2005 | Toki et al. |
| 2006/0036167 | A1* | 2/2006 | Shina .................. A61B 6/481 600/433 |
| 2006/0173297 | A1 | 8/2006 | Popescu |
| 2006/0206032 | A1* | 9/2006 | Miele ................ A61B 8/0858 600/481 |
| 2006/0241465 | A1 | 10/2006 | Huennekens et al. |
| 2007/0092056 | A1* | 4/2007 | Flohr .................. A61B 6/482 378/4 |
| 2007/0167833 | A1 | 7/2007 | Redel et al. |
| 2007/0276214 | A1* | 11/2007 | Dachille ............... G16H 30/40 600/407 |
| 2008/0199059 | A1 | 8/2008 | Eck et al. |
| 2009/0247864 | A1* | 10/2009 | Rauscher-Scheibe ...................... A61B 6/507 600/431 |
| 2009/0324047 | A1 | 12/2009 | Jaisch |
| 2010/0241404 | A1 | 9/2010 | Taylor et al. |
| 2012/0041739 | A1 | 2/2012 | Taylor |

OTHER PUBLICATIONS

Singh (the role of computational fluid dynamics in the management of unruptured intracranial aneurysm) (Year: 2009).*

Bogdahn, U., MD; et al.; "Transcranial Color-Coded Real-time Sonography in Adults", Stroke by American Heart Association 1990;21:1680-1688, 1990.

Antiga, Luca, Ph.D.; "Patient-Specific Modeling of Geometry and Blood Flow in Large Arteries", Politecnico Di Milano, 1999-2002, 190 pages.

Taylor, Charles A., et al.; "Experimntal and Computational Methods in Cardiovascular Fluid Mechanics", Annual Review of Fluid Mechanics, vol. 35, 2004, 42 pages.

Warmuth, Carsten, et al.; "Dynamic Spin Labeling Angiography in Extracranial Carotid Artery Stenosis", American Journal of Neuroradiology 25:1035-1043, May 2005.

Singh, Pankaj K., et al.; "The Role of Computational Fluid Dynamics in the Management of Unruptured Intracranial Aneurysms: A Clinicians' View", Computational Intelligence and Neyroscience, vol. 2009, Article ID 760364, 12 pages.

Botar, C.C., et al.; "Validation of CFD Simulation Results in Case of Portal Vein Blood Flow", 20th European Symposium on Conpute Aided Process Engineering, 2010, 6 pages.

* cited by examiner

SYSTEM AND METHOD FOR ESTIMATING VASCULAR FLOW USING CT IMAGING

CROSS-REFERENCE TO RELATED APPLICATION

This application is a divisional of U.S. patent application Ser. No. 13/425,724, entitled "SYSTEM AND METHOD FOR ESTIMATING VASCULAR FLOW USING CT IMAGING", filed Mar. 21, 2012, which is a non-provisional application of U.S. Provisional Patent Application No. 61/454,646, entitled "SYSTEM AND METHOD FOR ESTIMATING VASCULAR FLOW USING CT IMAGING", filed Mar. 21, 2011, which is herein incorporated by reference in its entirety for all purposes.

BACKGROUND OF THE INVENTION

Embodiments of the invention relate generally to diagnostic imaging and, more particularly, to a system and method of estimating hemodynamic information.

Non-invasive imaging technologies allow images of the internal structures or features of a patient to be obtained without performing an invasive procedure on the patient. In particular, such non-invasive imaging technologies rely on various physical principles, such as the differential transmission of x-rays through the target volume, measurement of resonant magnetic signals, or the reflection of acoustic waves, to acquire data and to construct images or otherwise represent the observed internal features of the patient.

For example, Coronary Computed Tomography Angiography (CCTA) is an imaging application that has evolved with the introduction and improvement of computed tomography (CT), an imaging technology based on the observed transmission of x-rays through the patient for a range of angular positions that is sufficient for image reconstruction. With the introduction of multi-slice CT scanners (e.g., 4-slice, 16-slice, 64-slice and so forth) and faster rotation speeds (e.g., about 0.35 seconds to about 0.5 seconds for a full gantry rotation), it has become possible to generate useful images of the heart. With current high-resolution (both spatial and temporal) 64-slice scanners, image quality is sufficient for CCTA to provide clinicians an imaging technique that has high negative predictive value (ratio of true negative classifications to the total number of negative classifications). In other words, the CCTA technology is very accurate in assessing patients that do not have disease. However, false positives may still occur at undesired frequency, reducing the positive predictive value of CCTA (ratio of true positive classifications to the total number of positive classifications). As such, advances are needed to improve the clinical utility of CCTA.

Further, CCTA typically provides only anatomical information of the heart and vascular structures. It may also be useful to provide various functional assessments, such as of territorial myocardial perfusion, which would be useful in determining if a narrowing in a coronary vessel (stenosis) due to atherosclerotic plaque is affecting cardiac function. There are various methods to assess cardiac function: treadmill stress test, stress echocardiogram, myocardial stress perfusion imaging (using Single Photon Emission Computed Tomography (SPECT)), Positron Emission Tomography (PET), CT perfusion, or invasive assessment of cardiovascular hemodynamics (fractional flow reserve (FFR)).

Combining both anatomical information and a correlated per territory assessment of resulting cardiac function may be useful in the clinical evaluation of cardiac disease. One approach, percutaneous coronary intervention (PCI), may provide this capability using anatomical information via projection coronary angiography and functional information through coronary blood pressure measurements from a transducer in the coronary vasculature. However, these procedures are highly invasive and frequently turn out to be unnecessary (diagnostic) (e.g., in approximately ⅓ of the procedures in patients with multi-vessel disease).

CT can be used to visualize localized narrowing of vessels, such as coronary arteries, cerebral arteries, or other vessels or arteries. The decision of whether or how to clinically intervene is often based on the assessed extent of the narrowing, such as the percentage reduction in the cross-sectional area compared with neighboring portions of the vessel. Some studies have shown that pressure measurements about the stenosis adds additional information beyond the percentage occlusion and can be used to estimate the functional impact of the stenosis and further differentiate the patient's treatment to improve the patient outcome over the treatment that would have been performed on the basis of the percentage occlusion alone.

Therefore, it would be desirable to design a system and method for estimating vascular flow that overcome the aforementioned drawbacks.

BRIEF DESCRIPTION OF THE INVENTION

According to an aspect of the invention, a computer readable storage medium having stored thereon a computer program comprising instructions, which, when executed by a computer, cause the computer to acquire a first set of data comprising anatomical information of an imaging subject, the anatomical information comprises information of at least one vessel. The instructions further cause the computer to process the anatomical information to generate an image volume comprising the at least one vessel, generate hemodynamic information based on the image volume, and acquire a second set of data of the imaging subject. The computer is also caused to generate an image comprising the hemodynamic information in combination with a visualization based on the second set of data.

According to another aspect of the invention, a method for estimating vascular hemodynamic information comprises acquiring data of an imaging subject, processing the acquired data to generate an image volume comprising anatomical information such as a vessel tree of the imaging subject, and determining anatomical information based on the image volume. The method also comprises generating hemodynamic information based on the vessel tree, acquiring an additional set of data of the imaging subject, and generating an image combining the hemodynamic information with image data based on the additional set of data.

According to yet another aspect of the invention, a CT system comprises a rotatable gantry having an opening to receive an object to be scanned, a high frequency electromagnetic energy projection source configured to project a high frequency electromagnetic energy beam toward the object, and a detector array having a plurality of detector cells configured to detect high frequency electromagnetic energy passing through the object. The CT system also comprises a data acquisition system (DAS) connected to the detector array and configured to receive outputs from the plurality of detector cells, an image reconstructor connected to the DAS and configured to reconstruct an image of the object from the detector cell outputs received by the DAS, and a computer. The computer is programmed to acquire a first set of data of an imaging subject, reconstruct an image volume based on the acquired data, and generate a vessel tree from the image volume. The computer is also programmed to process the vessel tree, generate hemodynamic information based on the processed vessel tree, obtain a second set of data of the imaging subject, and generate an image comprising the hemodynamic information in combination with a visualization based on the second set of data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of embodiments of the invention is described with respect to a multi-slice computed tomography (CT) system. Moreover, embodiments of the invention will be described with respect to the detection and conversion of x-rays. However, one skilled in the art will further appreciate that the invention is equally applicable for the detection and conversion of other high frequency electromagnetic energy. Embodiments of the invention will be described with respect to a "third generation" CT scanner, but is equally applicable with other CT system configurations.

Figure 1:
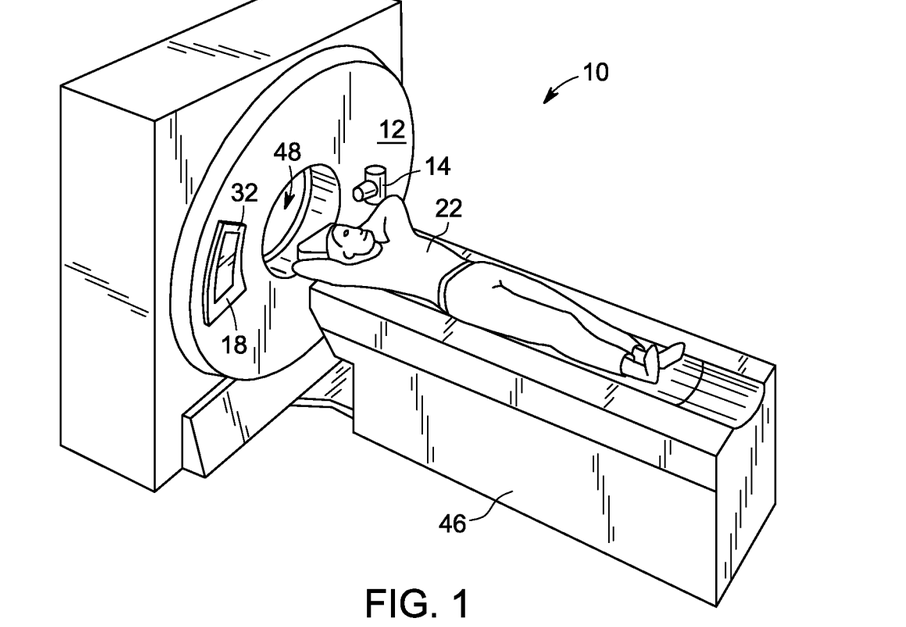
FIG. 1 is a pictorial view of a CT imaging system.
Figure 2:
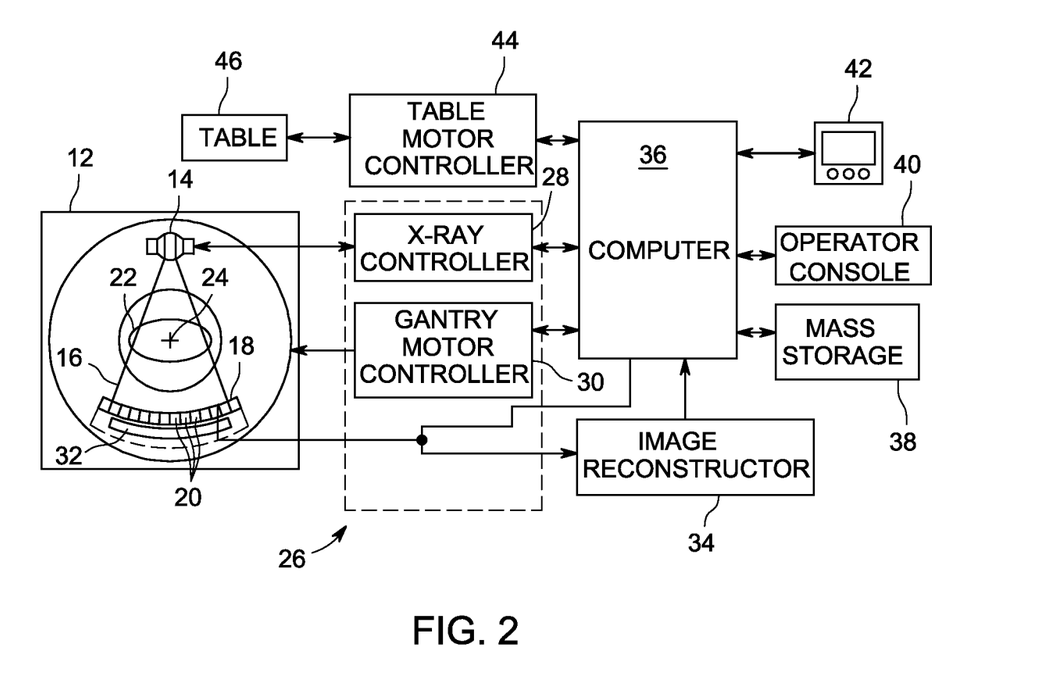
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly and/or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high-speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patient 22 through a gantry opening 48 of FIG. 1 in whole or in part.

Figure 3:
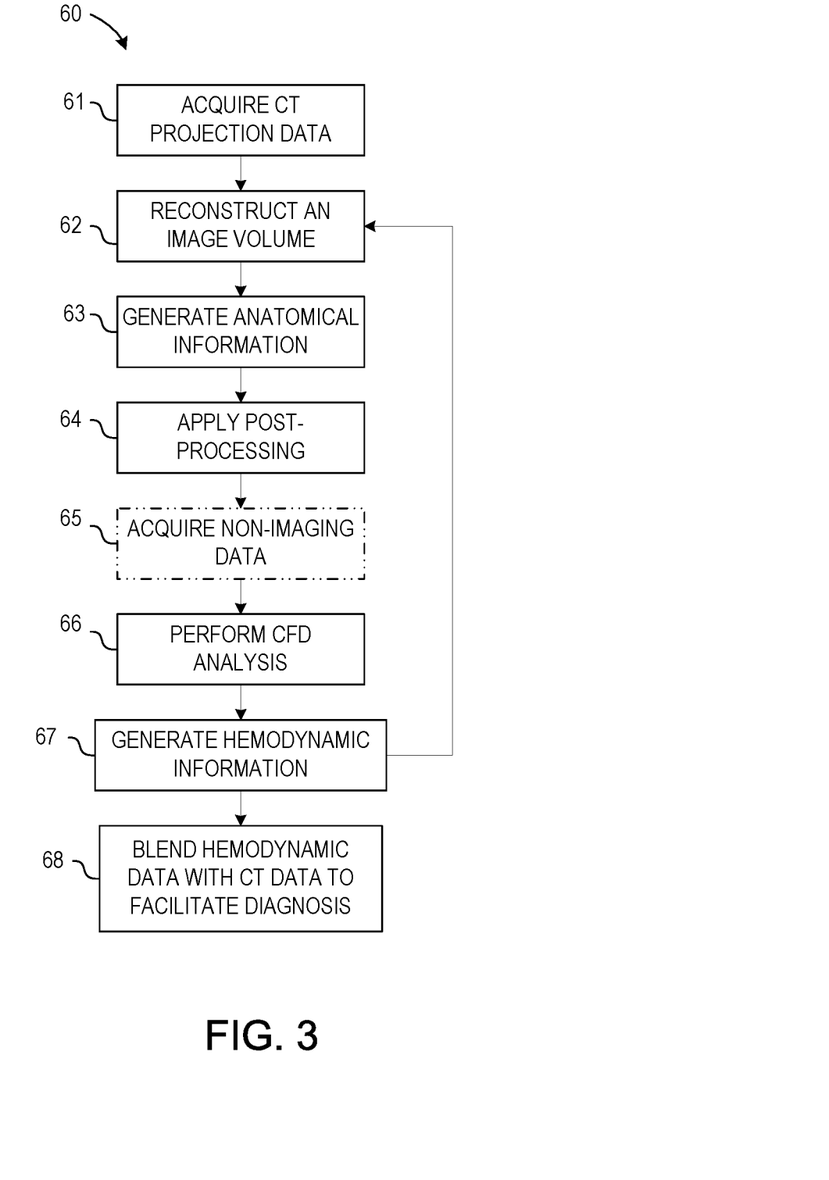
FIG. 3 is a flowchart illustrating a technique for calculating the fractional flow reserve (FFR) of an imaging subject according to an embodiment of the invention.

FIG. 3 illustrates a technique 60 for calculating hemodynamic information of an imaging subject according to an embodiment of the invention. CT projection data are acquired at block 61 and used to reconstruct an image volume at block 62, such as that described above with respect to FIGS. 1 and 2. The image volume may be generated using iterative or non-iterative reconstruction techniques in the case of x-ray-acquired projection data. In one embodiment, boundary conditions for subsequent FFR estimation may be generated using iterative reconstruction, where each reconstructed voxel in the image is modeled by two parameters: a DC component and a scaling for a basis function. The parameters are estimated based on the changes of measurement during the finite data acquisition time (e.g., a typical CT scan takes 0.35 s to acquire the full rotation of data). During this time period, the concentration of contrast has changed. By examining the projections over the reconstruction window, each voxel can be reconstructed as a function of time, instead of a simple average value. The function can be a simple speed (linear term) or speed and acceleration (linear and second order terms). These parameters provide dynamic information of the iodine concentration change and can then be used as the boundary conditions for the FFR estimation.

In another embodiment, the image volume reconstructed from x-ray-acquired imaging data may be combined with reconstructed image data from another imaging modality. For example, a first set of anatomical imaging data may be acquired using a CT imaging system as described above, and a second set may be acquired using, for example, an ultrasound imaging system, a magnetic resonance (MR) imaging system, and the like. The reconstructed image data from ultrasound or MR imaging systems may be used to enhance and/or adjust the x-ray-based image data. In addition or alternatively thereto, the first and second sets of data may both be used as inputs to the CFD analysis described below with respect to block 66.

At block 63, anatomical information or data of the imaging subject is generated from volumetric reconstructions. The anatomical information includes one or more vessels or systems of vessels of interest for which it is desired to perform an analysis to determine whether or not a stenosis exists and of the severity of the stenosis if it does exist. Vessel tree generation may include segmenting the vessels in the reconstructed image volume from other anatomical data or structures therein.

In one embodiment, the vessel tree generation includes automatic segmentation and representation of the vessel tree. In this embodiment, coronary arteries are automatically segmented, and a parametric representation of the shape and intensity profiles in the segmented coronary arteries is built. Such a representation allows differential analysis of the intensity values included in the segmented coronary artery volume with applications to flow-based measurements. For example, the intensity profile along the centerline allows for normalization of flow calculations along the centerlines. The segmented coronaries can also be represented as a sequence of 2D cross-sections perpendicular to the centerline or through a sequence of 3D spheres whose envelope defines the 3D segmentation. The 2D cross section or the 3D sphere are local unit descriptors encoding both shape and intensity information. The variations in shape and intensity along successive units are reflective of the flow dynamics of the coronary artery. In the most general case, these "shape particle"-based representations can be directly used as components in any shape analysis, including computational fluid dynamics calculations.

In another embodiment, the vessel tree generation includes efficient semi-automatic editing. That is, often, due to acquisition-induced artifacts or contrast inhomogeneities, segmentation methods may result in an incomplete 3D coronary volume on which computational fluid dynamics analysis for FFR map generation cannot be performed. Methods to complete the coronary volume in the absence of obvious lumen intensity information are therefore used. Shape-based tracking methods can be used (e.g., propagation from strong evidence to weak areas) or through robust sequential Monte Carlo methods to bridge gaps due to artifacts and absence of contrast. This can be combined with plaque detection methods to correctly identify vessel narrowing. Such a method can be completely automatic or cued by a few interactions with the user. A cleanup process that follows the tracking and segmentation steps can be applied to identify obvious artifacts in the segmented volume or surface such as external discontinuities not relevant to the structural integrity of the 3D coronary volume.

In another embodiment, the vessel tree generation includes performing a segmentation to identify a wall volume-of-interest around a contrast-enhanced lumen of the coronary arteries followed by detection and segmentation of the plaque. The plaque can be virtually subtracted, such as by using spectral information, for example, to compute hypothetical flow in the absence of the stenosis. Such a system can also be used to evaluate the effective benefit of a stent prior to performing a procedure to insert the stent. The calculation of the blood flow within the vasculature and pressure before and after a region of vessel narrowing allows for the calculation of whether or not there is a restriction, and whether or not there is a need for corrective actions to be pursued such as a stent or other corrective means.

As described below, the anatomical information is used in the calculation of a fractional flow reserve (the pressure distal to the stenosis divided by the pressure proximal to the stenosis) of the vessel or vessel system of interest. The acquired anatomical information may be combined with one or more of the following embodiments and input into computational fluid dynamics (CFD) model to help provide high-fidelity hemodynamic information to further assess the disease state of the vessel or system of vessels.

In one embodiment, the lumen size of vessel of interest may be measured proximal to, throughout, and distal to the stenosis. The lumen size may be measured with or without a contrast agent and may be included in the data input into the CFD model. In addition, a model of the lumen size measurement error may be incorporated in the data input into the CFD model.

In another embodiment, the anatomical information may be generated from imaging data acquired using multiple energy levels. That is, the x-ray source of the CT system may be operated or toggled at two or more kVp levels to acquire two or more sets of imaging data. The multiple sets of imaging data may then be used to estimate the material composition of the tissue at the region of interest. The two or more sets of imaging data at multiple kVp levels may be acquired during separate scans for each kVp level, during a single scan using fast-kVp switching, or using a single kVp setting and an energy sensitive detector (photon-counting, energy-discriminating detector).

In another embodiment, the anatomical information may be generated from additional imaging data, which are reconstructed using existing data. The properties of the reconstruction algorithm (both analytical and iterative reconstruction algorithms) may be modified to achieve a particular objective. For instance, high-resolution structures in the image may be accentuated, as is needed to generate high-fidelity anatomical information (dimension of normal and/or diseased vasculature). Alternatively, the reconstruction algorithm may be modified to reduce noise in the image to improve the fidelity of tissue characterization, either using standard single-energy images or material-specific, multi-energy images. Other representations of the anatomy, such as monochromatic images generated using multi-energy techniques, which reduce image artifacts, may also be used. Although not meant to be limiting, the examples listed above provide additional information that may improve the fidelity of hemodynamic information generated using CFD models.

In another embodiment, the anatomy of the imaging subject may be tagged with a contrast agent or other similar agent. The tagged anatomy may then be analyzed to estimate a stiffness or compliance of the tissue of interest or to estimate a change in lumen diameter.

In another embodiment, a multi-energy scout (two-dimensional projection of scanned anatomy) may be performed using a contrast agent. In this manner, the anatomical information may highlight the vascular data.

In another embodiment, the CT imaging scan to acquire the anatomical information may incorporate focal spot wobbling techniques (improving the sampling or projection data, thereby reducing aliasing artifacts) to yield imaging data with high spatial resolution.

In another embodiment, the anatomical information may be generated from imaging data acquired at multiple phases of cardiac cycle of the imaging subject. The data from the multiple phases may be averaged or weighted for estimation of the size of the vessel of interest. The CT scanner may acquire data at multiple phases of the cardiac cycle, which may also include applying a motion compensation technique to reduce motion-induced artifacts in the acquired imaging data, thereby providing imaging data to generate high-fidelity anatomical information.

In another embodiment, the anatomical information may be generated from imaging data acquired at multiple dilations of the vasculature. For example, a first imaging scan may acquire the imaging data to generate anatomical information at a first dilation, and the second imaging scan may acquire the imaging data to generate additional anatomical information at a second dilation greater than the first dilation. In addition, modalities such as ultrasound or magnetic resonance (MR) may be used to acquire velocities before and after vasodilation to measure or estimate the coronary flow reserve.

In another embodiment, the anatomical information may be generated from imaging data acquired at multiple stress levels. In this manner, anatomical data may be generated from imaging data acquired at various heart rates. Data may be acquired at a normal or resting heart rate, and various stress levels may be induced either pharmacologically or with exercise, to acquire the data at high or low heart rates and at various functional states of imaged tissue, as appropriate.

Post-processing may be applied at block 64 prior to calculating additional hemodynamic information using a CFD model. An embodiment of post-processing may include reducing the blooming from the calcium (or other material) that can obscure the lumen. Using multiple energy data acquired as described above, the effects of calcium (or other material) may be estimated and used to reduce or eliminate the blooming effect that may lead to mis-estimation of the size of the lumen near the calcium.

In another embodiment, the multiple energy data may also be used to find areas of plaque and to estimate the type and proportion of localized plaque.

Another embodiment of post-processing may include accurately estimating the point spread function (PSF) for each reconstruction process. The PSF may be used to further adjust the lumen size measurements fed into the CFD model to estimate the flow information. That is, the final lumen size is adjusted based on the based on the initial measurement and the PSF factor, which is obtained based on the reconstruction filter (for filtered backprojection), reconstruction voxel size, and other post-processing steps.

Another embodiment of post-processing may include correcting motion-induced artifacts caused by motion during the acquisition of the anatomical information.

Another embodiment of post-processing may include calculating constraints for the CFD model based on the identification of the relative material density and composition of the wall tissue surrounding or forming the vessels or coronary lumens determined by multi-material decomposition of multi-energy acquired data.

Another embodiment of post-processing may include acquiring estimates of measurement errors from each modality or from multiple acquisitions of the same modality so that multiple measurements can be statistically combined to generate a measurement with reduced error.

While the post-processing of block 64 has been described above as being subsequent to generation of the anatomical information at block 63, embodiments of the invention envision that post-processing of the reconstructed image volume may occur prior to generation of the vessel tree.

As shown in phantom, an embodiment of the invention includes acquiring non-imaging data (e.g., electrocardiogram data or other functional data) at block 65. The non-imaging data may be used as an input to the CFD analysis as described below with respect to block 66.

Still referring to FIG. 3, at block 66, a CFD analysis is performed and an hemodynamic information is generated at block 67 (including blood flow, blood pressure, etc.). Although not limiting, one example of hemodynamic information is the estimation of the pressure along the vasculature, which allows computation of the FFR at constricted regions along the vasculature that are suspicious. The FFR map presents pressure ratios throughout at least a portion of the vessel tree and allows a stenosis to be analyzed for diagnosis and treatment. The pressure proximal to, throughout, and distal to the stenosis may be used in such analysis.

In addition to inputting the post-processed vessel tree data into the CFD model, other data can also be input to the CFD model to influence generation of hemodynamic information. For example, in one embodiment, information about the prior treatment of the vessel of interest at a stenosis location, such as the presence of a stent or a previous angioplasty, may be included. In another embodiment, estimates of the pressure at the aortic root or coronary ostia, which may be estimated by measuring brachial or radial artery pressures and using systems modeling to account for the pressure wave propagation and reflection, may be included. In another embodiment, the non-imaging data acquired at block 65 may be included. Furthermore, in another embodiment, information about blood flow in some of the arterial branches may be used to facilitate computation of boundary conditions.

According to another embodiment, noise may be estimated for each voxel and for each projection sample during iterative reconstruction. The information can be used to guide the CFD computations. Voxels with lower noise can be given a higher confidence level during the CFD analysis. By utilizing the weighting factor, the accuracy of the hemodynamic can be improved.

In another embodiment, the noise estimation may be performed prior to image reconstruction. That is, by utilizing the variance estimation of each projection sample, the variance of the reconstructed image (e.g., using filtered backprojection) can be accurately predicted. This information can be used to provide guidance to the CFD process.

In another embodiment, a Coronary Computed Tomography Angiography (CCTA) exam may be used to acquire volumes at multiple different phases of the cardiac cycle. Segmenting each of these volumes and then matching them enables a correspondence map between the various volumes to be calculated or determined that can be used as an input to the CFD process to assist in the computation of flow approximations in local hemodynamic information as a function of the intensity distribution of a sub-volume of the vasculature (for example, coronaries) across the phases.

In another embodiment, demarcation of plaque can be factored into wall-induced strains on the lumen surface and its effect on blood flow. Flow calculations during the CFD process can include using the wall segmentation (not just the lumen surface).

After generating the hemodynamic information at block 67, additional data may be acquired and combined or blended with the hemodynamic information at block 68 for visualizing and/or analyzing the character of a stenosis to assist with diagnosis and treatment of any stenosis found. The additional data may be ancillary data not used to generate the image volume or used in the calculation of the hemodynamic information. In one embodiment, the additional data may be, for example, perfusion measurements, such as made by measuring contrast agent uptake rate, peak concentration, or washout rate, or other perfusion-related parameters, either at rest or at stress perfusion, or both. Single-energy or multi-energy CT data may be used to estimate the myocardial perfusion. Other types of additional data that may be acquired are discussed below with respect to blending the hemodynamic data therewith.

In one embodiment, a perfusion study may be performed to gather perfusion data in tissues adjacent to the vessel tree. For example, the perfusion data can indicate if a normal or reduced amount of flow is going through the myocardium. A stenosis followed by a large ischemic area of the myocardium or other tissue adjacent to a stenosis can indicate a reduced blood flow, which may indicate that the absolute pressure drop across the stenosis is reduced. These parameters may be incorporated into a model (static or adaptive) to estimate the morphologic and clinical significance of the stenosis and may, together with anatomical information, indicate the type of intervention for addressing the stenosis. For example, the intervention may include determining whether to insert a stent or to perform angioplasty based on the presence or extent of localized calcium. Moreover, all available anatomical (CT image data) and functional (perfusion, blood flow, blood pressure, FFR, vessel wall motion, etc.) information may be used in a statistical classifier to increase the confidence in determining whether or not the suspected lesion is causal of ischemia (oxygen deprivation in the tissue).

In another embodiment, locations of stenosis lesions from CCTA can be bookmarked with image series. Lesions can be highlighted and displayed on a 3D vessel tree. Coronary vessels can also be mapped to corresponding myocardial regions (e.g., such as using a 17-segment model). Perfusion information can be color fused on a 3D heart volume rendering on the "surface" of the myocardium or other tissue for simultaneous viewing of the vessel tree together with the tissue perfusion information. Additional hemodynamic information (blood flow, blood pressure, FFR) can be integrated into these views where, for example, the lumen of each coronary vessel (within a volume rendering or reformat image) can be color-coded to represent the continuous hemodynamic information along a given vessel.

Figure 4:
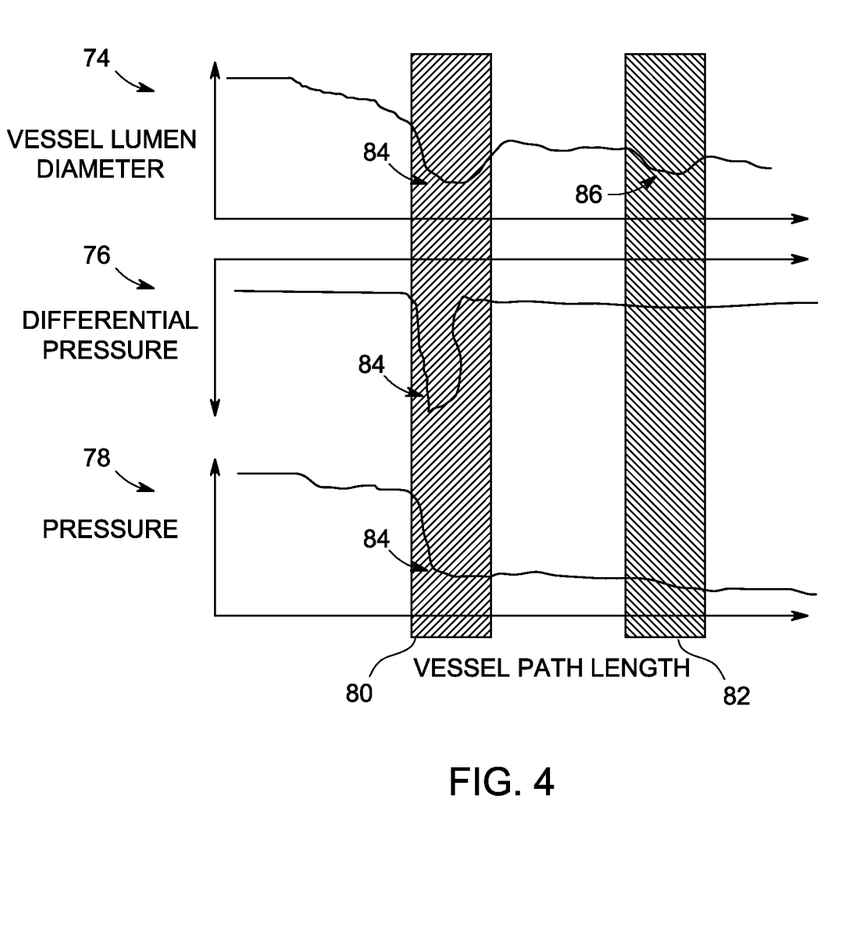
FIG. 4 shows exemplary curves based on vessel and FFR data according to an embodiment of the invention.

Likewise, as shown in FIG. 4, a vessel diameter measurement (or lumen cross-sectional area measurements or stenosis ratio) versus vessel path length (proximal to distal) plot 74 may be generated and displayed with correlated and corresponding curves showing hemodynamic information (shown as pressure) versus vessel path length plot 78 and showing differential hemodynamic information (shown as differential pressure) versus vessel path length plot 76. These curves 74-78, plotted alongside each other, may be annotated with highlighted areas of correlation 80 or of disagreement 82. Although shown as differential hemodynamic information 76, alternate information such as relational hemodynamic information (for example, ratios of pressure estimates) may be shown. Correlated local minimums 84 (i.e., a positive finding for both Coronary CTA and computational FFR) or any mismatched local min 86 (i.e., such as a false positive from CCTA alone), may be used to aid diagnosis and therapy planning. Selection of one of the highlighted regions 80, 82 on the curves may cause a mapping to a corresponding lesion in the 3D volume and to the corresponding myocardial region within the 3D volume to be indicated or shown. In addition, a mapping to a standard bull's-eye plot of myocardial perfusion data can be displayed as well. For example, referring to FIGS. 4 and 5, selection of highlighted regions 80, 82 may cause the corresponding regions 88, 90 on a bull's-eye plot 92 to be indicated and shown.

In addition, a "filet view" (visualization of the vessel by determining its axis and generating a radial profile of the vessel) of the curved reformatted vessel may be used to overlay the hemodynamic information. The "filet view" may help improve the showing of the soft plaque and remodeling. Also, overlay layers of visualized information on the display device can be used; these layers can be turned on and off to show or hide the hemodynamic information overlay for comparison with a non-overlay view.

Figure 5:
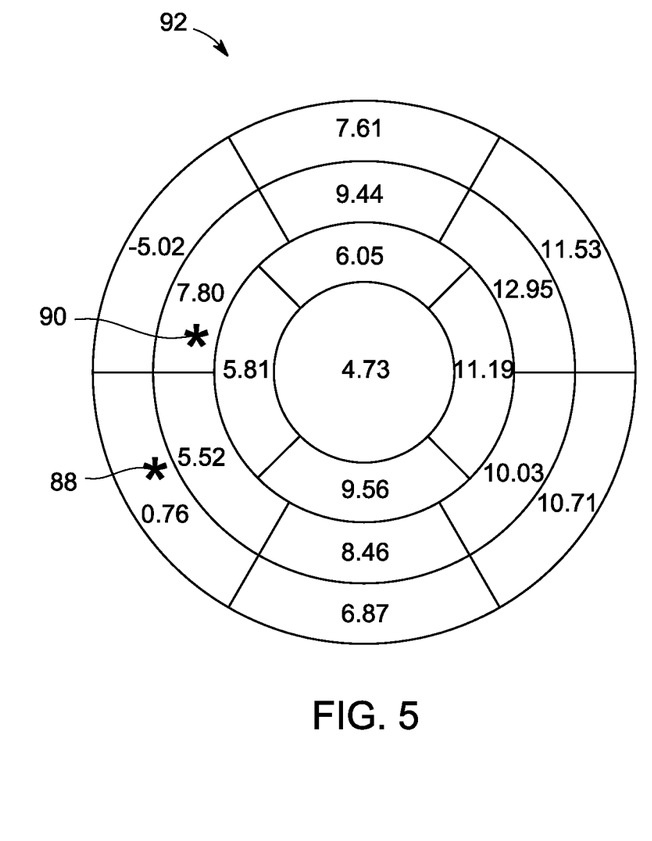
FIG. 5 is a bull's-eye plot according to an embodiment of the invention.
Figure 6:
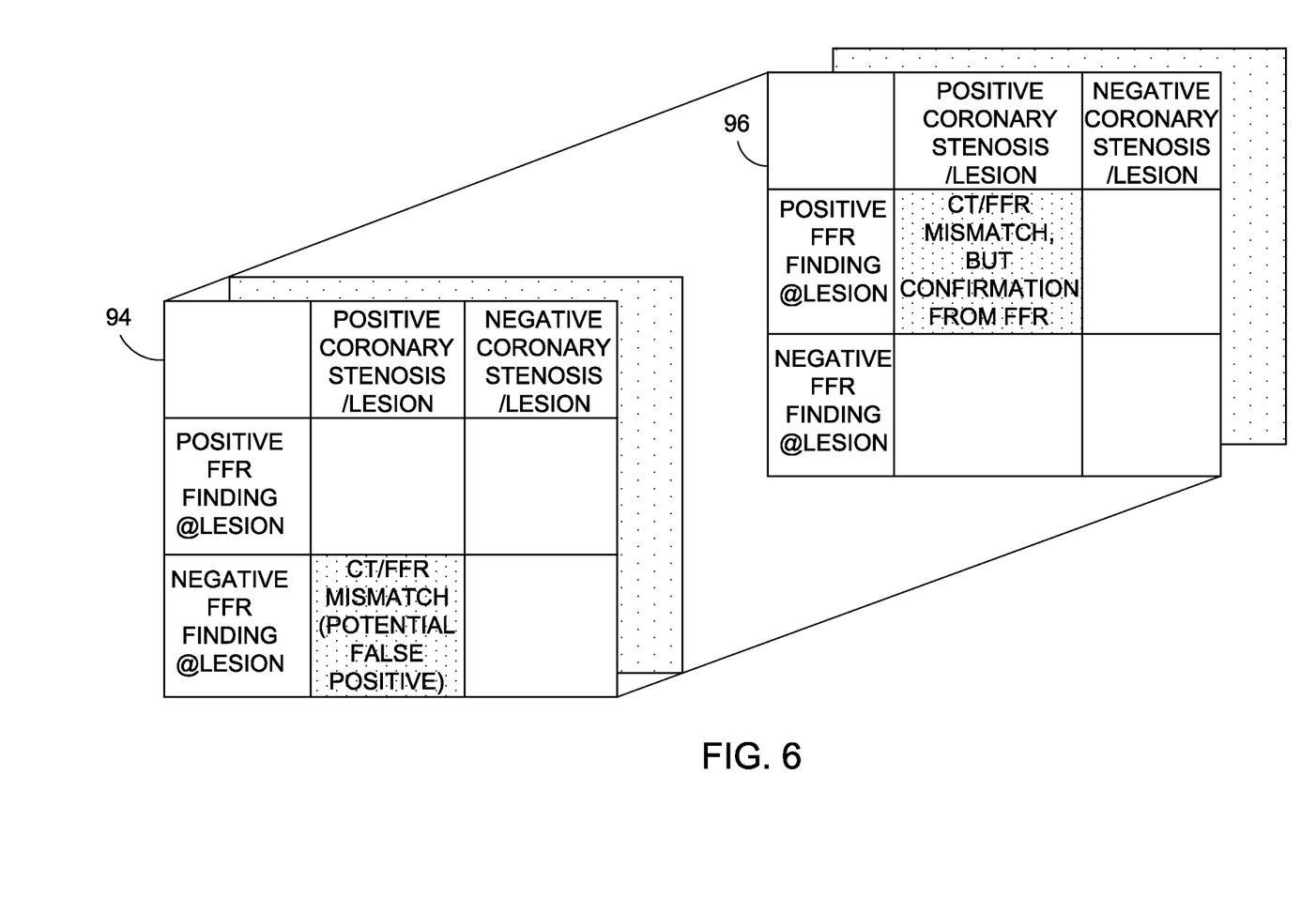
FIG. 6 is a graphical and tabulated data analysis according to an embodiment of the invention.

If rest/stress CT perfusion information is available, a 3-way data analysis (anatomical data, perfusion data, and hemodynamic data) showing correlation and mismatches can also be highlighted and analyzed. For example, FIG. 6 shows a multi-dimensional, graphical and tabulated data analysis according to an embodiment of the invention. A first table 94 may show positive perfusion defects within a corresponding myocardial region, and a second table 96 may show negative perfusion defects within a corresponding myocardial region. First table 94 may include a list of lesions (or myocardial regions) that are "positive" from at least one test (i.e., CCTA, CT Perfusion, FFR, or other exam) while second table 96 may include a list of lesions (or myocardial regions) that are "negative" from at least one test. Correlations and/or mismatches may be highlighted. If the correlated or mismatched areas are selected, the actual locations within the integrated exam data may be shown and indicated. In another embodiment, rather than presenting the "list" of lesions/findings in a tabular format as shown in FIG. 5, the lesions may be presented more graphically—on a vessel map "schematic", on a textbook illustration type rendering presentation, or integrated into the actual CT derived 3D vessel tree itself.

According to an embodiment of the invention, information that cannot be provided by hemodynamic information (such as areas of positive remodeling, coronary vessel wall information, cardiac function, etc.) can also be integrated into the comprehensive presentation for visualization and reporting.

Still referring to block 68 of FIG. 3, the additional data may include calculation of a severity of the stenosis as well as calculation of the confidence measure of the data related to the stenosis. The severity and confidence measure may be presented numerically or graphically. The confidence measure may be assisted by the incorporation of the calcium score. In one example, colors may be applied to numbers on the images, or semi-transparent color overlays may be used. The calculations may be performed by a host processor of the imaging system, or on a remote processor. The calculations may be entirely algorithmic or may include degree of human interaction. The algorithm may include finding the vessels of interest within the volume(s) of data, or vessels may be manually identified by a user. Regions of localized stenosis to be analyzed may be algorithmically determined, or may be manually identified by a user.

In another embodiment, the characterization of plaque can be color coded on a volume-rendered vessel tree or on 3D MIP (maximum intensity projection)/reformat views (cross-section, curved reformat lumen view, etc.) following vessel tracking.

Additional functionality that can be provided in an embodiment of the invention includes advanced display which combines lumen shape, wall/plaque densities, and functional or other maps; correct coronary opacification and other methods to normalize uptake, values, etc. (providing more consistent lumen HU values that have been normalized for CT contrast flow rate data for example); and a means of measuring flow from dynamic x-ray projection images, including taking into account the 3D shapes reconstructed from the system.

In another embodiment as shown in FIG. 3, after the hemodynamic information is generated at block 67, process control of technique 60 may return to block 62 for a revised reconstruction of the image volume based on the hemodynamic information obtained at block 67. That is, based on the hemodynamic information, it may be desirable to revise one or more parameters of the reconstruction process of block 62. For example, the reconstruction kernel, the field-of-view (FOV), or other parameters may be modified or revised to improve the reconstructed image volume. Thereafter, the re-processing of blocks 63-67 using the improved image volume may increase the quality of the generated hemodynamic information.

A technical contribution for the disclosed method and apparatus is that it provides for a computer implemented system and method of estimating vascular flow.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a computer readable storage medium having stored thereon a computer program comprising instructions, which, when executed by a computer, cause the computer to acquire a first set of data comprising anatomical information of an imaging subject, the anatomical information comprises information of at least one vessel. The instructions further cause the computer to process the anatomical information to generate an image volume comprising the at least one vessel, generate hemodynamic information based on the image volume, and acquire a second set of data of the imaging subject. The computer is also caused to generate an image comprising the hemodynamic information in combination with a visualization based on the second set of data.

According to another embodiment of the invention, a method for estimating vascular hemodynamic information comprises acquiring data of an imaging subject, processing the acquired data to generate an image volume comprising anatomical information such as a vessel tree of the imaging subject, and determining anatomical information based on the image volume. The method also comprises generating hemodynamic information based on the vessel tree, acquiring an additional set of data of the imaging subject, and generating an image combining the hemodynamic information with image data based on the additional set of data.

According to yet another embodiment of the invention, a CT system comprises a rotatable gantry having an opening to receive an object to be scanned, a high frequency electromagnetic energy projection source configured to project a high frequency electromagnetic energy beam toward the object, and a detector array having a plurality of detector cells configured to detect high frequency electromagnetic energy passing through the object. The CT system also comprises a data acquisition system (DAS) connected to the detector array and configured to receive outputs from the plurality of detector cells, an image reconstructor connected to the DAS and configured to reconstruct an image of the object from the detector cell outputs received by the DAS, and a computer. The computer is programmed to acquire a first set of data of an imaging subject, reconstruct an image volume based on the acquired data, and generate a vessel tree from the image volume. The computer is also programmed to process the vessel tree, generate hemodynamic information based on the processed vessel tree, obtain a second set of data of the imaging subject, and generate an image comprising the hemodynamic information in combination with a visualization based on the second set of data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:
utilizing a processor to:
   acquire a set of multi-energy data using a CT imaging system, wherein the set of multi-energy data comprises information of at least one vessel of interest of an imaging subject;
   process the set of multi-energy data to derive a derived relative material density and composition of at least one of wall tissue and lumen of the at least one vessel of interest to generate a processed data set;
   generate an enhanced vessel tree comprising the at least one vessel of interest using the processed data set;
   perform a computational fluid dynamics (CFD) analysis on the enhanced vessel tree to generate localized hemodynamic information of the at least one vessel of interest; and
   generate an image of the at least one vessel of interest comprising the localized hemodynamic information derived from the enhanced vessel tree.

2. The method of claim 1, comprising utilizing the processor to:
   acquire the set of multi-energy data via a plurality of focal spots of the x-ray tube;
   acquire the set of multi-energy data at multiple phases of a cardiac cycle of the imaging subject; and
   acquire the set of multi-energy data at multiple stress levels of the imaging subject.

3. The method of claim 1, comprising utilizing the processor to:
   acquire an additional set of data of the imaging subject via the CT imaging system or an imaging system of a different imaging modality than the CT imaging system; and
   generate the image comprising the hemodynamic information in combination with a visualization from the additional set of data.

4. The method of claim 3, comprising utilizing the processor to:

acquire perfusion data of a tissue of the imaging subject adjacent to the at least one vessel; and generate the image comprising the hemodynamic information in combination with a visualization of the perfusion data generated from the additional set of data.

5. The method of claim 4, comprising utilizing the processor to:

calculate a first representation comprising vessel lumen diameter data versus vessel path length data;

calculate a second representation comprising hemodynamic information versus vessel path length data;

calculate a third representation comprising information from the additional set of data versus vessel path length data; and simultaneously display the first representation, the second representation, and the third representation to a user.

6. The method of claim 1, comprising utilizing the processor to:

generate the enhanced vessel tree cause the computer to generate the enhanced vessel tree by characterizing and segmenting one or more tissue types in the at least one vessel in the set of multi-energy data from other anatomical structures contained therein.

7. The method of claim 1, wherein, based on the derived relative material density and composition of at least one of the wall tissue and the lumen of the at least one vessel, the processor is further utilized to:

reduce blooming from calcium in the at least one vessel;

correct motion-induced artifacts in the at least one vessel;

identify plaque in the at least one vessel; or estimate a point spread function and adjust at least one of the wall tissue and lumen sizes of the at least one vessel based on the point spread function.

8. The method of claim 1, comprising utilizing the processor to:

locate a vessel of interest based on one of the enhanced vessel tree and the hemodynamic information; and locate and characterize a stenosis within the vessel of interest.

9. The method of claim 8, comprising utilizing the processor to:

calculate a severity value of the stenosis based on one or more of anatomical information and hemodynamic information related to the stenosis; and display the severity value to a user.

10. The method of claim 1, comprising utilizing the processor to generate hemodynamic information cause the computer to generate blood pressure information of the at least one vessel.

11. The method of claim 1, comprising utilizing the processor to input into the computational fluid dynamics (CFD) analysis the enhanced vessel tree of the at least one vessel generated from the processed data set and a set of non-imaging data.

12. The method of claim 1, comprising utilizing the processor to generate the image as a plot of the hemodynamic information displayed alongside a lumen diameter plot of the at least one vessel.

13. The method of claim 1, comprising utilizing the processor to generate the image having highlighted therein areas of at least one of correlation and disagreement between anatomical information of the at least one vessel and the hemodynamic information.

14. The method of claim 1, comprising utilizing the processor to:

revise a revised processing parameter based on the hemodynamic information; and reprocess the processed data set using the revised processing parameter.

15. The method of claim 1, comprising utilizing the processor to calculate at least one constraint of the computational fluid dynamics (CFD) analysis using the at least one of the material density and the composition of the at least one vessel.

* * * * *